US012797433B2

(12) United States Patent
Nam et al.

(10) Patent No.: US 12,797,433 B2
(45) Date of Patent: Nov. 17, 2026

(54) COMPOSITION FOR IMPROVING RESPIRATORY HEALTH CONTINUOUSLY EXPOSED TO PARTICULATE MATTER ATMOSPHERE

(71) Applicant: AMOREPACIFIC CORPORATION, Seoul (KR)

(72) Inventors: Hyunjin Nam, Yongin-si (KR); Juewon Kim, Yongin-si (KR); Miyoung Park, Yongin-si (KR); Kyoungmi Jung, Yongin-si (KR); Jinoh Chung, Yongin-si (KR); Gyeyoung Choi, Yongin-si (KR); Wanki Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 132 days.

(21) Appl. No.: 18/442,847

(22) Filed: Feb. 15, 2024

(65) Prior Publication Data

US 2024/0180993 A1 Jun. 6, 2024

Related U.S. Application Data

(62) Division of application No. 17/341,868, filed on Jun. 8, 2021, now Pat. No. 11,938,163.

(30) Foreign Application Priority Data

Jun. 9, 2020 (KR) ........................ 10-2020-0069891
May 12, 2021 (KR) ........................ 10-2021-0061491

(51) Int. Cl.

| | |
|---|---|
| ***A61K 36/82*** | (2006.01) |
| ***A23L 2/52*** | (2006.01) |
| ***A23L 33/00*** | (2016.01) |
| ***A23L 33/105*** | (2016.01) |
| ***A61K 9/00*** | (2006.01) |
| ***A61K 31/353*** | (2006.01) |
| ***A61P 7/00*** | (2006.01) |
| ***A61P 11/16*** | (2006.01) |

(52) U.S. Cl.

CPC ................ *A61K 36/82* (2013.01); *A23L 2/52* (2013.01); *A23L 33/105* (2016.08); *A23L 33/40* (2016.08); *A61K 9/0056* (2013.01); *A61K 31/353* (2013.01); *A61P 7/00* (2018.01); *A61P 11/16* (2018.01); *A23V 2002/00* (2013.01); *A61K 2236/33* (2013.01); *A61K 2236/331* (2013.01); *A61K 2236/333* (2013.01)

(58) Field of Classification Search

None

See application file for complete search history.

(56) References Cited

U.S. PATENT DOCUMENTS

2008/0113044 A1 5/2008 Alberte et al.

FOREIGN PATENT DOCUMENTS

| | | | |
|---|---|---|---|
| JP | 5192380 | B2 | 2/2009 |
| KR | 10-2002-0006132 | A | 1/2002 |
| KR | 10-2008-0006691 | A | 1/2008 |
| KR | 10-2010-0026835 | A | 3/2010 |
| KR | 10-2016-0079459 | A | 7/2016 |
| KR | 10-2018-0127488 | A | 11/2018 |
| KR | 10-2019-0044303 | A | 4/2019 |
| WO | 2007/029982 | A1 | 3/2007 |
| WO | 2017/174718 | A1 | 10/2017 |

OTHER PUBLICATIONS

Al-Basher (Saudi Journal of Biological Sciences (2019), vol. 26, pp. 531-540—published online on Aug. 18, 2017).*

Hamed (J Physiol Biochem (2010), vol. 66, pp. 143-151).*

"Amorepacific Vitalbeautie Launches 'METAGREEN' Upgrade", Article, Asiatoday (2019) with English Abstract.

Key-Hwa Lim et al., "Review of Effectiveness of Green Tea Epigallocatechin Gallate (EGCG) on the Inside and Outside of Human Body", Kor. J. Aesthet. Cosmetol., vol. 13(6): 701-711, 2015.

Philip L. Leopold et al., "Smoking is Associated with Shortened Airway Cilia", PLoS (2009), vol. 4, No. 12, e8157.

R.S. Pappas, Ph.D., "Toxic Elements in Tobacco and in Cigarette Smoke: Inflammation and Sensitization"; Metallomics (2011), vol. 3, No. 11, pp. 1181-1198.

Juewon Kim et al., "Application of Green Tea Catechins, polysaccharides, and flavonol prevent fine dust induced bronchial damage by modulating inflammation and airway cilia", Scientific Reports (Jan. 2021), 11:2232.

(Continued)

*Primary Examiner* — Susan Hoffman

(74) *Attorney, Agent, or Firm* — Merchant & Gould P.C.

(57) ABSTRACT

An aspect of the present disclosure relates to a composition for improving respiratory health exposed to particulate matter, which contains a green tea extract, a green tea polysaccharide and a green tea flavonol as active ingredients. The composition provided in an aspect of the present disclosure can improve respiratory health damaged by exposure to particulate matter by enhancing the effect of preventing adsorption of particulate matter to bronchial epithelial cells and activating the cilia of bronchial epithelial cells. The composition provided in an aspect of the present disclosure may decrease blood heavy metal level.

5 Claims, 5 Drawing Sheets

(56) References Cited

OTHER PUBLICATIONS

Markus Braun et al., "Particulate Matter Emissions of Four Different Cigarette Types of One Popular Brand: Influence of Tobacco Strength and Additives", Int. J. Environ. Res. Public Health (2019), vol. 16, 263, 11 pages.
Wajdy Al-Awaida et al., "Chinese Green Tean Consumption Reduces Oxidative Stress, Inflammation and Tissues Damage in Smoke Exposed Rats", Iranian Journal of Basic Medical Sciences (2014), vol. 17, pp. 740-746.
Juewon Kim et al., "Combination of green tea catechins, polysaccharides, and flavonols against urban fine dust particle-induced bronchial damage mediated by modulation of inflammation factors and airway cilia", Research Square, Apr. 10, 2020, pp. 1-24.
Office Action issued for Korean Patent Application No. 10-2021-0061491, date of mailing: Sep. 26, 2025, 4 pages including machine translation.

* cited by examiner

COMPOSITION FOR IMPROVING RESPIRATORY HEALTH CONTINUOUSLY EXPOSED TO PARTICULATE MATTER ATMOSPHERE

CROSS-REFERENCE TO RELATED APPLICATION

This application is a Divisional Application of U.S. patent application Ser. No. 17/341,868, filed Jun. 8, 2021, now U.S. Pat. No. 11,938,163, which claims the priority of Korean Patent Application No. 10-2020-0069891, filed on Jun. 9, 2020, and Korean Patent Application No. 10-2021-0061491, filed on May 12, 2021, the contents of which in their entirety are herein incorporated by reference.

TECHNICAL FIELD

The present disclosure relates to a composition for improving respiratory health continuously exposed to particulate matter atmosphere and a method for improving respiratory health exposed to particulate matter.

BACKGROUND ART

Recently, concerns about particulate matter as environmental issue are increasing. Since particulate matter has a very small particle size as compared to yellow dust, etc., it penetrates deeper into the human body and is harmful to the human body because it includes more harmful substances such as heavy metals, nitrates, ammonium salts, sulfates, etc. Although there are various definitions and classifications of particulate matter, it is generally classified into $PM_{2.5}$ (<2.5 μm, ultrafine particles) and $PM_{10}$ (<10 μm, coarse particles) based on particle size. The World Health Organization (WHO) evaluates air pollution based on this criterion.

Especially, particulate matter is highly associated with respiratory diseases, and causes aggravation of lung inflammatory responses and respiratory symptoms, increased drug use, increased hospitalization and death rate in the short term. In the long term, it increases lower respiratory symptoms, decreases pulmonary function, aggravates asthma and chronic obstructive pulmonary disease (COPD), and increases lung cancer.

Unlike respiratory or pulmonary damage by bacteria or temporary intoxication, particulate matter cannot be easily controlled by the immunity of the human body and the particulate matter that has entered the respiratory tract cannot be discharged forcibly. In addition, it is uncertain what problem will occur when due to such damage. Accordingly, development of a composition capable of improving respiratory health damaged by particulate matter is necessary.

DISCLOSURE

Technical Problem

In an aspect, the present disclosure is directed to providing a composition capable of improving respiratory health exposed to particulate matter and a method for improving respiratory health exposed to particulate matter.

Technical Solution

In an aspect, the present disclosure provides a method for improving respiratory health exposed to particulate matter, which includes a step of administering an effective amount of a composition comprising a green tea extract, a green tea polysaccharide and a green tea flavonol to a subject in need of improvement of respiratory health exposed to particulate matter.

In an exemplary embodiment, the green tea extract may contain catechin.

In an exemplary embodiment, a daily administration dosage of catechin by the green tea extract may be 0.3-1.0 g.

In an exemplary embodiment, the green tea extract may be an extract of water, an organic solvent or a mixture solvent thereof.

In an exemplary embodiment, the green tea flavonol may include one or more selected from a group consisting of myricetin, quercetin and kaempferol.

In an exemplary embodiment, a weight ratio of the green tea extract, the green tea polysaccharide and the green tea flavonol may be 10:0.1-9:0.01-9.

In an exemplary embodiment, the particulate matter may contain one or more of arsenic, cadmium, lead, nickel and mercury.

In an exemplary embodiment, the particulate matter may have a particle size of $PM_{10}$ or smaller.

In an exemplary embodiment, the improvement of respiratory health exposed to particulate matter may be achieved by increase in the number of cilia of bronchial epithelial cells and activation of the cilia.

In an exemplary embodiment, the composition may be a food composition.

In an exemplary embodiment, the composition may be a pharmaceutical composition.

In another aspect, the present disclosure provides a method for lowering blood heavy metal level, which includes a step of administering an effective amount of a composition containing a green tea extract, a green tea polysaccharide and a green tea flavonol to a subject in need of lowering blood heavy metal level.

Advantageous Effects

In an aspect, a composition provided by the present disclosure may improve respiratory health exposed to particulate matter.

In an aspect, the composition provided by the present disclosure may enhance the effect of preventing adsorption of particulate matter to bronchial epithelial cells.

In an aspect, the composition provided by the present disclosure may increase the number of cilia of bronchial epithelial cells and activate the cilia.

In an aspect, the composition provided by the present disclosure may decrease blood heavy metal level.

BEST MODE

Figure 1:
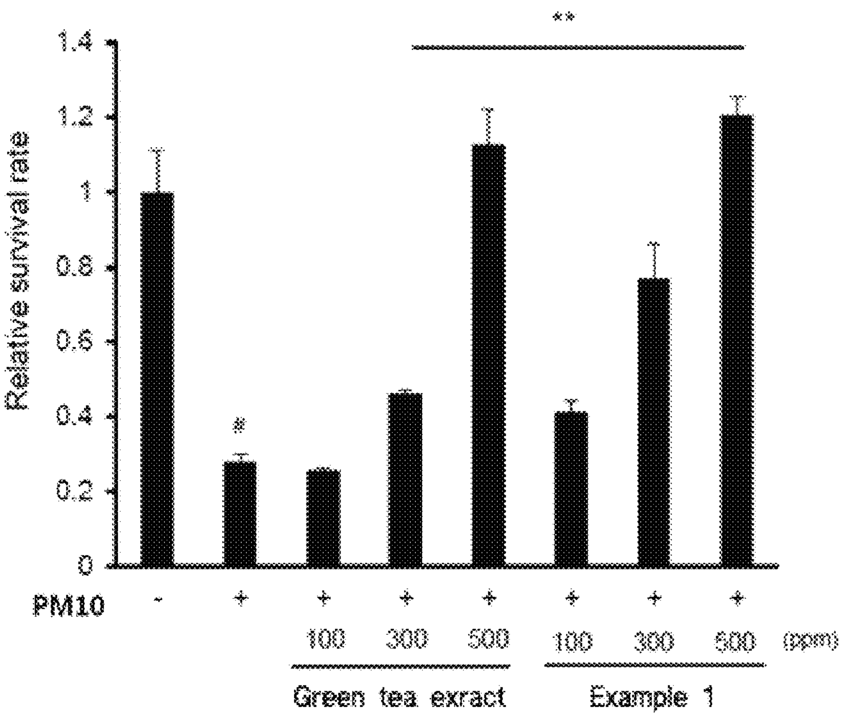
FIG. 1 shows the survival rate of bronchial epithelial cells treated with a green tea extract, a green tea polysaccharide and a green tea flavonol according to an exemplary embodiment of the present disclosure.

Hereinafter, the present disclosure is described in detail.

In an aspect, the present disclosure provides a composition for improving respiratory health exposed to particulate matter, which contains a green tea extract, a green tea polysaccharide and a green tea flavonol as active ingredients.

In the present disclosure, "green tea" refers to *Camellia sinensis* belonging to the family Theaceae. Both dried and undried green may be used without limitation in type or days of cultivation. Also, in the present disclosure, the green tea is not limitation in its part (stem, leaf, flow or seed). Specifically, the leaf of green tea may be used.

In the present disclosure, the "green tea extract" includes an extract extracted from *Camellia sinensis* belonging to the family Theaceae, regardless of extraction method, extraction solvent, extracted ingredient or type of the extract, an extract extracted from tea leaf fermented by inoculating with *Bacillus subtilis* spp. or fermented naturally, and a fraction obtained by fractionating the extract with a specific solvent. The tea includes one or more selected from a group consisting of the leaf, flower, stem and seed of tea tree, specifically the leaf. In addition, the extract may be specifically in powder form. The extraction or fractionation may be performed using water, an organic solvent or a mixture solvent thereof. The organic solvent may be an alcohol, isopropanol, acetone, hexane, ethyl acetate, carbon dioxide or a mixture solvent thereof, although not being limited thereto. The extraction or fractionation may be performed at room temperature or elevated temperature under a condition where the active ingredients of green tea are not destroyed or the destruction is minimized. The alcohol may be a $C_1$-$C_5$ lower alcohol. The number or method of the extraction or fractionation is not specially limited. For example, methods such as cold precipitation extraction, ultrasonic extraction, reflux condensation extraction, hot water extraction, etc. may be used. Specifically, after extracting or fractionating active ingredients by cold precipitation or heating, the filtrate may be concentrated under reduced pressure to obtain the green tea extract of the present disclosure.

In the present disclosure, the "green tea polysaccharide" refers to a polysaccharide derived from a green tea extract, which is produced by binding of a sugar produced from photosynthesis with an amino acid. The green tea polysaccharide may be prepared by a method known in the art, without special limitation.

In another aspect, the present disclosure provides a composition for lowering blood heavy metal level, which contains a green tea extract, a green tea polysaccharide and a green tea flavonol as active ingredients.

In an exemplary embodiment, the green tea extract may contain catechin. The catechin may be one or more selected from a group consisting of (−)-epicatechin (EC), (−)-epigallocatechin (EGC), (−)-epicatechin gallate (ECG) and (−)-epigallocatechin gallate (EGCG).

In an exemplary embodiment, a daily administration dosage of catechin by the green tea extract may be 0.3-1.0 g, and a daily administration dosage of (−)-epigallocatechin gallate (EGCG) may be 300 mg or less. If the daily administration dosage of catechin is less than 0.3 g, it may be difficult to attain the effect of the present disclosure. And, a daily administration dosage of EGCG exceeding 300 mg may cause liver damage. Specifically, the daily administration dosage of catechin by the green tea extract may be 0.3 g or more, 0.31 g or more, 0.32 g or more, 0.33 g or more, 0.34 g or more, 0.35 g or more, 0.36 g or more, 0.37 g or more, 0.38 g or more, 0.39 g or more, 0.40 g or more, 0.41 g or more, 0.42 g or more, 0.43 g or more, 0.44 g or more, 0.45 g or more, 0.46 g or more, 0.47 g or more, 0.48 g or more, 0.49 g or more or 0.5 g or more, and 1.0 g or less, 0.99 g or less, 0.98 g or less, 0.97 g or less, 0.96 g or less, 0.95 g or less, 0.94 g or less, 0.93 g or less, 0.92 g or less, 0.91 g or less, 0.90 g or less, 0.89 g or less, 0.88 g or less, 0.87 g or less, 0.86 g or less, 0.85 g or less, 0.84 g or less, 0.83 g or less, 0.82 g or less, 0.81 g or less, 0.80 g or less, 0.79 g or less, 0.78 g or less, 0.77 g or less, 0.76 g or less, 0.75 g or less, 0.74 g or less, 0.73 g or less, 0.72 g or less, 0.71 g or less or 0.70 g or less.

In an exemplary embodiment, the green tea extract may be an extract of water, an organic solvent or a mixture solvent thereof. The water may include distilled water or purified water, and the organic solvent may include one or more selected from a group consisting of an alcohol, isopropanol, acetone hexane, ethyl acetate and carbon dioxide, although not being limited thereto. The alcohol may be a $C_1$-$C_5$ lower alcohol.

In an exemplary embodiment, the green tea flavonol may include one or more selected from a group consisting of myricetin, quercetin and kaempferol.

In an exemplary embodiment, a weight ratio of the green tea extract, the green tea polysaccharide and the green tea flavonol may be 10:0.1-9:0.01-9. Specifically, the weight ratio of the green tea extract, the green tea polysaccharide and the green tea flavonol may be 10:0.1-9:0.01-9, 10:0.1-7:0.01-7, 10:0.5-7:0.05-7, 1:0.5-5:0.05-5, 10:1-5:0.1-5, 10:1-3:0.1-3 or 10:1:1. If the weight ratio of the green tea extract, the green tea polysaccharide and the green tea flavonol is outside the above ranges, the effect of improving respiratory health exposed to particulate matter may decrease.

In the present disclosure, "particulate matter" refers to very small particulate materials not visible to the eyes, which float or scatter in the atmosphere for a long time. Specifically, the particulate matter may have a particle size with a diameter of 10 μm or smaller ($PM_{10}$), more specifically 2.5 μm or smaller ($PM_{2.5}$). The particulate matter with a particle diameter of 2.5 μm or smaller ($PM_{2.5}$) is called "ultrafine particles". In the present disclosure, the "particulate matter" is intended to include the "ultrafine particles".

In an aspect, the particulate matter may include one or more of arsenic, cadmium, lead, nickel and mercury. Heavy metals such as the arsenic, cadmium, lead, nickel, mercury, etc. included in the particulate matter may aggravate respiratory health by attacking respiratory organs such as bronchi, etc.

In an exemplary embodiment, the composition may activate the cilia of bronchial epithelial cells. In the present disclosure, the activation of the cilia of bronchial epithelial cells may mean increasing the number and length of the cilia.

In an exemplary embodiment, the composition may decrease blood heavy metal level.

In an exemplary embodiment, the administration route of the composition may be oral administration, although not being limited thereto.

In an exemplary embodiment, the composition may be a food composition. The composition may be formulated into, for example, a, tablet, a granule, a pill, a powder, a liquid such as a drink, a caramel, a gel, a bar, a tea bag, etc., although not being specially limited thereto. The food composition of each formulation may be prepared adequately by those skilled in the art without difficulty by mixing ingredients commonly used in the art in addition to the active ingredient depending on purposes. When the active ingredient is used in combination with other ingredients, a synergistic effect may occur.

In an exemplary embodiment, the food composition may contain various nutrients, vitamins, minerals (electrolytes), flavorants such as synthetic flavorants, natural flavorants, etc., colorants, extenders (cheese, chocolate, etc.), pectic acid and its salts, alginic acid and its salts, organic acid, protective colloidal thickeners, pH control agents, stabilizers, antiseptic, glycerin, alcohols, carbonating agents used in carbonated beverages, etc. In addition, the food composition according to an exemplary embodiment may contain pulp for preparation of natural fruit juice, fruit juice drinks and vegetable drinks. These ingredients may be used either independently or in combination. The content of these additives is of no great importance but, in general, may be about 0-50 parts by weight based on 100 parts by weight of the composition according to an exemplary embodiment.

In an exemplary embodiment, the composition may be a pharmaceutical composition. The pharmaceutical composition may be administered orally or parenterally, e.g., rectally, topically, transdermally, intravenously, intramuscularly, intraperitoneally, subcutaneously, etc. Formulations for oral administration may include a tablet, a pill, a soft or hard capsule, a granule, a powder, a fine granule, a liquid, an emulsion or a pellet, although not being limited thereto. Formulations for parenteral administration may include a solution, a suspension, an emulsion, a gel, an injection, a medicinal drip, a suppository, a patch or a spray, although not being limited thereto. The formulations may be prepared easily according to common methods in the art, and may further contain a surfactant, an excipient, a wetting agent, an emulsification accelerator, suspension, a salt or buffer for control of osmotic pressure, a colorant, a flavor, a stabilizer, an antiseptic, a preservative or other commonly used adjuvants.

In another aspect, the present disclosure provides a use of a green tea extract, a green tea polysaccharide and a green tea flavonol for preparation of a composition for improving respiratory health exposed to particulate matter.

In another aspect, the present disclosure provides a method for improving respiratory health exposed to particulate matter, which includes administering an effective amount of a composition containing a green tea extract, a green tea polysaccharide and a green tea flavonol to a subject in need of improvement of respiratory health exposed to particulate matter In another aspect, the present disclosure provides a use of a green tea extract, a green tea polysaccharide and a green tea flavonol for preparation of a composition for lowering blood heavy metal level.

In another aspect, the present disclosure provides a method for lowering blood heavy metal level, which includes administering an effective amount of a composition containing a green tea extract, a green tea polysaccharide and a green tea flavonol to a subject in need of lowering blood heavy metal level.

Hereinafter, the present disclosure will be described in more detail through examples, etc. The examples are only for illustrating the present disclosure, and it will be obvious to those having ordinary knowledge in the art that it should not be interpreted that the scope of the present disclosure is limited by the examples.

[Preparation Example 1] Preparation of Green Tea Extract 100 kg of green tea leaf (*Camellia sinensis*, Jeju O'sulloc Farm) was extracted at 70-90° C. for 1-2 hours by adding 1,000-1,500 L of 70% fermenting ethyl alcohol or purified water. After lowering the temperature of the sample to room temperature and filtering the same, a green tea extract was prepared by concentrating the obtained solution and spray-drying the same.

[Preparation Example 2] Preparation of Green Tea Polysaccharide

A residue obtained after preparation of the green tea extract of Preparation Example 1 was extracted with 90° C. hot water for 3 hours under stirring. After separating the residue from the filtrate by filtration with filter cloth and centrifugation, the separated filtrate was concentrated to 1/10 the volume of purified water. Then, after adding 95% ethanol dropwise thereto, a green tea polysaccharide was obtained by hot-air drying the same.

[Preparation Example 3] Preparation of Green Tea Flavonol

After reacting the green tea extract of Preparation Example 1 (1% w/v, aqueous solution, pH 5.0) with 1% (v/v) tannase (500 units/mL) at 40° C. for 14 hours in a thermoshaker (Eppendorf, Germany), the reaction was terminated by heating at 90° C. for 20 minutes. This is to provide maximized effect by highly concentrating the contents of myricetin, quercetin and kaempferol by effectively hydrolyzing the flavonol glycosides in the green tea extract to aglycons.

[Example 1] Preparation of Mixture of Green Tea Extract, Green Tea Polysaccharide and Green Tea Flavonol A mixture of a green tea extract, a green tea polysaccharide and a green tea flavonol was prepared by mixing the green tea extract of Preparation Example 1, the green tea polysaccharide of Preparation Example 2 and green tea flavonol of Preparation Example 3 at a weight ratio of 10:1:1.

[Test Example 1] Evaluation of Survival Rate of Bronchial Epithelial Cells

Human bronchial epithelial cells (BEAS-2B cell line, CRL-9609) were divided into 4 groups (control, particulate matter, green tea extract and Example 1). The bronchial epithelial cells of the particulate matter group were treated with particulate matter ($PM_{10}$, 100 μg/mL) for 24 hours, and the bronchial epithelial cells of the green tea extract group and the Example 1 group were treated respectively with the green tea extract of Preparation Example 1 and the mixture of a green tea extract, a green tea polysaccharide and a green tea flavonol of Example 1 at 100, 300 or 500 μg/mL for 48 hours and then with particulate matter ($PM_{10}$ 100 μg/mL) for 24 hours. Then, cell survival rate was measured by MTT assay, and the result is shown in FIG. 1. Airborne particular matter reference material ERM-CZ100 ($PM_{10}$-like) was used as the particulate matter, and the control group was untreated.

As can be seen from FIG. 1, whereas the cell survival rate was significantly increased in the groups treated with the green tea extract at 300 and 500 μg/mL as compared to the particulate matter group, it was significantly increased in all the groups treated with Example 1 at 100, 300 and 500 μg/mL as compared to the particulate matter group.

Figure 2:
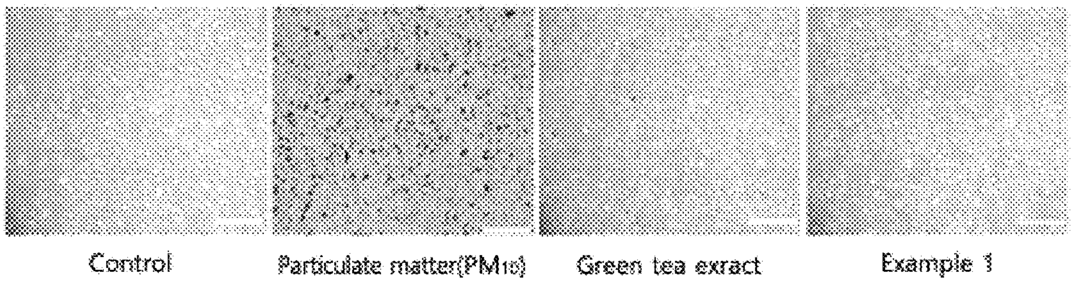
FIG. 2 shows the effect of preventing adsorption of particulate matter of a green tea extract, a green tea polysaccharide and a green tea flavonol according to an exemplary embodiment of the present disclosure.

[Test Example 2] Evaluation of Effect of Preventing Adsorption of Particulate Matter Human bronchial epithelial cells (BEAS-2B cell line) were divided into 4 groups (control, particulate matter, green tea extract and Example 1). The bronchial epithelial cells of the green tea extract group and the Example 1 group were treated respectively with the green tea extract of Preparation Example 1 and the mixture of a green tea extract, a green tea polysaccharide and a green tea flavonol of Example 1 at 300 μg/mL for 48 hours and then with particulate matter ($PM_{10}$, 100 μg/mL) for 24 hours. Then, the particulate matter adsorbed to the bronchial epithelial cells was observed by microscopic imaging (SZX16; Olympus, Japan). The result is shown in FIG. 2. The control group was untreated.

As can be seen from FIG. 2, the black particulate matter was adsorbed to the surface of the human bronchial epithelial cells in the particulate matter group. In contrast, the adsorption of the particulate matter was not observed in the bronchial epithelial cells treated with Example 1, showing that Example 1 has superior effect of preventing adsorption of particulate matter.

Figure 3A:
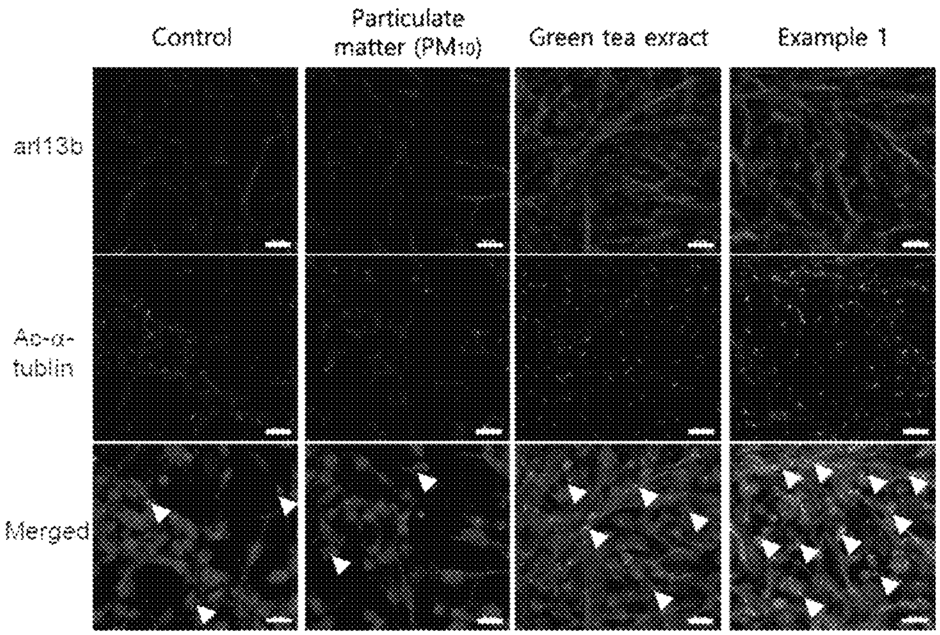
FIGS. 3A-3C show the effect of activating the cilia of bronchial epithelial cells of a green tea extract, a green tea polysaccharide and a green tea flavonol according to an exemplary embodiment of the present disclosure.
Figure 3B:
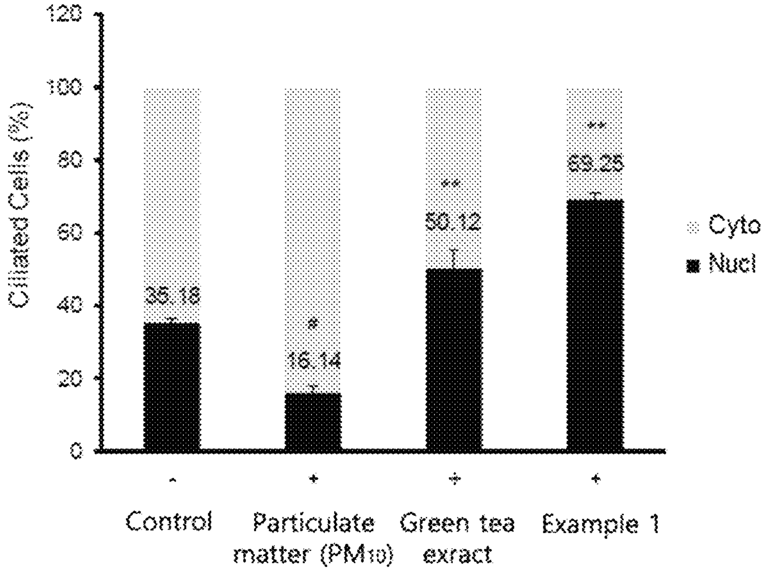
Figure 3C:
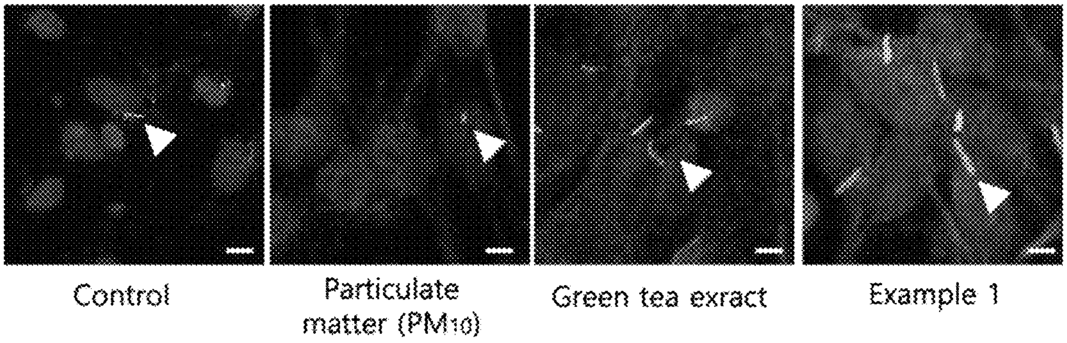

[Test Example 3] Evaluation of Activation of Cilia of Human Bronchial Epithelial Cells Human bronchial epithelial cells (BEAS-2B cell line) were divided into 4 groups (control, particulate matter, green tea extract and Example 1). The bronchial epithelial cells of the green tea extract group and the Example 1 group were treated respectively with the green tea extract of Preparation Example 1 and the mixture of a green tea extract, a green tea polysaccharide and a green tea flavonol of Example 1 at 300 μg/mL for 48 hours. Then, after treating with particulate matter ($PM_{10}$, 100 μg/mL) for 24 hours, the activation of the cilia of the bronchial epithelial cells was observed. The result is shown in FIGS. 3A-3C. The control group was untreated. The four test groups treated with each test substance and particulate matter were subjected to fixation with 4% paraformaldehyde for 30 minutes, washing, treatment with 0.1% Triton X-100 for 10 minutes, washing and incubation with a primary antibody (anti-acetylated tubulin antibody, Sigma-Aldrich; anti-ARL13B antibody, Proteintech) at 4° C. overnight. Then, after treating with a secondary antibody (Alexa Fluor 555- or Alexa Fluor 488-conjugated goat anti-rabbit or anti-mouse antibody) at room temperature for 1 hour, the result was visualized with a confocal laser scanning microscope (LSM700, Carl Zeiss).

In FIG. 3A, arl13b indicates cilia-membrane protein, Ac-α-tublin indicates acetylated alpha tubulin, corresponding to cilia which are microtubule-based cellular organelles, and the white triangles in the merged images indicate the cilia stained with DAPI. FIG. 3B shows the increased percentage of ciliated cells based on the total cells in the merged figures of FIG. 3A. In FIG. 3C, the white triangles indicate the increase of the length of the cilia.

From FIGS. 3A-3C, it can be seen that, whereas the number and length of cilia were decreased in the particulate matter group treated only with particulate matter, the length and number of cilia were increased in the group treated with the green tea extract as compared to the particulate matter group. Particularly, the length and number of cilia were increased distinctly in the group treated with Example 1 as compared to the green tea extract group.

Figure 4:
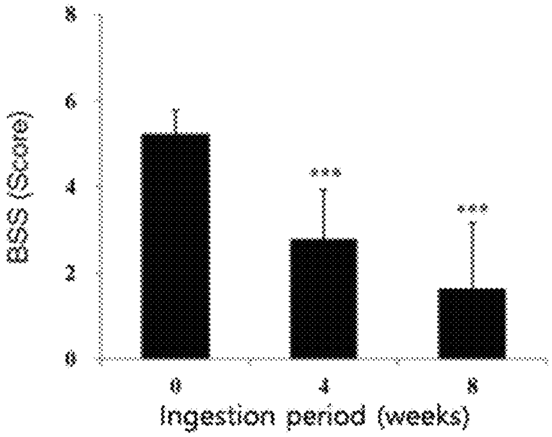
FIG. 4 shows the effect of improving the severity of bronchitis by particulate matter of a green tea extract, a green tea polysaccharide and a green tea flavonol according to an exemplary embodiment of the present disclosure.

[Test Example 4] Evaluation of Severity of Acute Bronchitis in People Continuously Exposed to Particulate Matter Atmosphere For investigation of the effect of improving severity of acute bronchitis of Example 1, bronchitis severity score was evaluated for those having jobs exposed to particulate matter. Thirty four people who had worked at environments exposed to particulate matter at least 4 hours a day for 3 months or longer (e.g., street cleaners, drivers, traffic guides, parking guides, stall keepers, delivery servicemen, etc.) were selected. The selected 34 people were asked to ingest Example 1 for 8 weeks and score their severity of cough, sputum, dyspnea, chest pain on coughing and dry rales (from 0=absent to 4=very severe). The result is shown in FIG. 4.

As a result, it was confirmed that the severity of acute bronchitis was decreased significantly at week 4 as compared to before the ingestion of Example 1. In addition, it was confirmed that the severity of acute bronchitis was improved in 94% of the people (32 out of 34) at week 8 after the ingestion. In particular, cough, sputum and dyspnea were decreased significantly.

Figure 5:
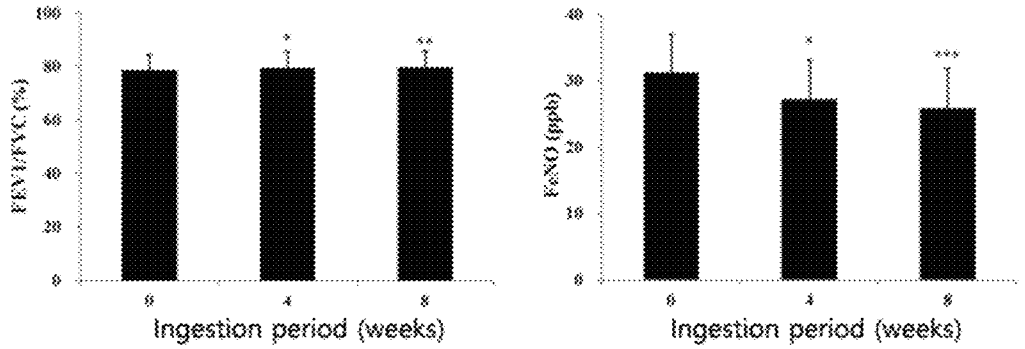
FIG. 5 shows a result of investigating the effect of a green tea extract, a green tea polysaccharide and a green tea flavonol according to an exemplary embodiment of the present disclosure on pulmonary function by particulate matter by measuring airway obstruction (FEV1/FVC, %) and severity of inflammation (FeNO, fractional exhaled nitric oxide).

[Test Example 5] Evaluation of Lung Function (FEV1/FVC) and Fractional Exhaled Nitric Oxide (FeNO) in People Continuously Exposed to Particulate Matter Atmosphere The 34 people selected in Test Example 4 were asked to ingest Example 1 for 8 weeks, and FEV1/FVC lung function test and fractional exhaled nitric oxide (FeNO) measurement for assessment of airway inflammation were conducted. The result is shown in FIG. 5.

As a result, it was confirmed that lung function (FEV1/FVC) was improved significantly at week 4 after the ingestion as compared to before the ingestion of Example 1. At week 8 after the ingestion, the lung function was significantly improved in 64.7% of the people (22 out of 34). In addition, fractional exhaled nitric oxide (FeNO) was decreased significantly from week 4 after the ingestion, and was decreased significantly in 67.7% of the people (23 out of 34) at week 8.

Figure 6:
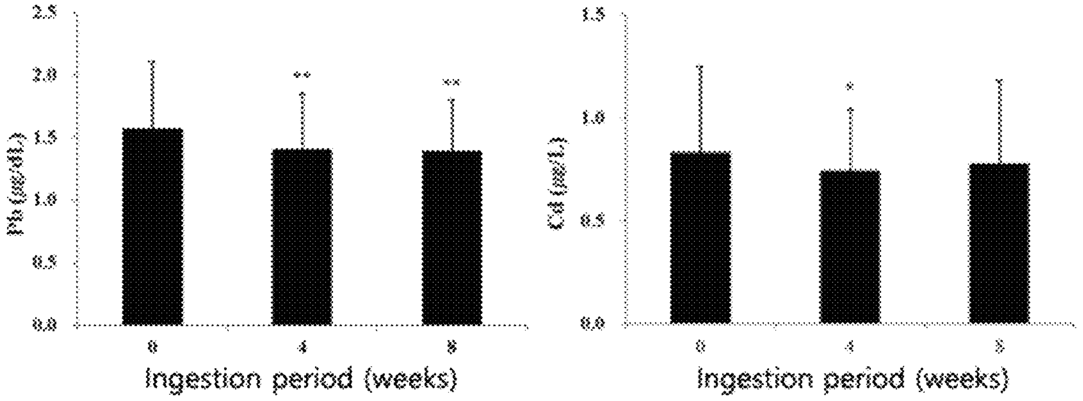
FIG. 6 shows the effect of a green tea extract, a green tea polysaccharide and a green tea flavonol according to an exemplary embodiment of the present disclosure on improvement of blood heavy metal level by particulate matter.

[Test Example 6] Measurement of Blood Heavy Metal Level in People Continuously Exposed to Particulate Matter Atmosphere The 34 people selected in Test Example 4 were asked to ingest Example 1 for 8 weeks and the change in the blood level of heavy metals (lead and cadmium) was measured. The result is shown in FIG. 6.

As a result, it was confirmed that blood lead level was significantly decreased at weeks 4 and 8 after the ingestion as compared to the baseline before the ingestion of Example 1. At week 8, the blood lead level was decreased in 70.6% (24 out of 34). In addition, blood cadmium level was significantly decreased at week 4, and was decreased in 64.7% (22 out of 34) at week 8.

[Test Example 7] Evaluation of Questionnaires on Respiratory Health for People Continuously Exposed to Particulate Matter Atmosphere The 34 people selected in Test Example 4 were asked to ingest Example 1 for 8 weeks and chronic obstructive pulmonary disease assessment (CAT, COPD assessment test), Leicester cough questionnaire (LCQ) assessment and bronchiectasis health questionnaire (BHQ) assessment were conducted. The result is shown in FIG. 7.

Figure 7:
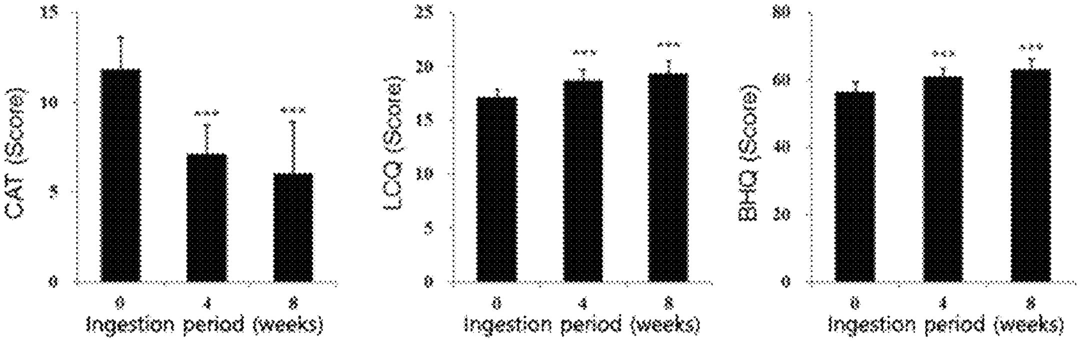
FIG. 7 shows a result of conducting chronic obstructive pulmonary disease assessment, Leicester cough questionnaire assessment and bronchiectasis health questionnaire assessment by particulate matter for a green tea polysaccharide and a green tea flavonol according to an exemplary embodiment of the present disclosure.

As can be seen from FIG. 7, the scores of all the chronic obstructive pulmonary disease assessment, the Leicester cough questionnaire assessment and the bronchiectasis health questionnaire assessment were significantly improved from week 4 after the ingestion as compared to the baseline before the ingestion of Example 1. At week 8, the respiratory symptoms were improved in 100% (34 out of 34), 94.1% (32 out of 34) and 97.1% (33 out of 34) of the subjects, respectively.

[Formulation Example 1] Tablet

After mixing 1 g of the green tea extract of Preparation Example 1, 0.1 g of the green tea polysaccharide of Preparation Example 2, 0.1 g of the green tea flavonol of Preparation Example 3, 0.4 g of maltitol, 60 mg of lactose and 140 mg of cornstarch and preparing into a granule using a fluidized-bed dryer, a table was prepared using a tablet-making machine.

[Formulation Example 2] Capsule

After mixing 1 g of the green tea extract of Preparation Example 1, 0.1 g of the green tea polysaccharide of Preparation Example 2, 0.1 g of the green tea flavonol of Preparation Example 3, 0.1 g of L-carnitine, 0.18 g of soybean oil, 0.02 g of palm oil, 0.08 g of hydrogenated vegetable oil and 0.06 g of lecithin, a capsule was prepared according to a common method by filling the mixture in a capsule.

[Formulation Example 3] Powder

After mixing 1 g of the green tea extract of Preparation Example 1, 0.1 g of the green tea polysaccharide of Preparation Example 2, 0.1 g of the green tea flavonol of Preparation Example 3, 0.5 g of lactose and 0.5 g of cornstarch, a powder was prepared by filling the mixture in a sealed pouch.

[Formulation Example 4] Granule

After mixing 1 g of the green tea extract of Preparation Example 1, 0.1 g of the green tea polysaccharide of Preparation Example 2, 0.1 g of the green tea flavonol of Preparation Example 3, 25 g of anhydrous crystalline glucose and 55 g of starch and preparing into a granule using a fluidized-bed granulator, the prepared granule was filled in a pouch.

[Formulation Example 5] Liquid

After dissolving 1.5 g of the green tea extract of Preparation Example 1, 0.2 g of the green tea polysaccharide of Preparation Example 2, 0.2 g of the green tea flavonol of Preparation Example 3, 5 g of high-fructose corn syrup and 2.5 g of mannitol in an adequate amount of purified water according to a common method, lemon flavor was added and the total volume was adjusted to 100 mL. The prepared liquid was filled in a brown bottle.

[Formulation Example 6] Spray

A spray was prepared according to a common method with to the composition described in Table 1.

TABLE 1

| Ingredients | Contents |
|---|---|
| Green tea extract of Preparation Example 1 | 1000 mg |
| Green tea polysaccharide of Preparation Example 2 | 100 mg |
| Green tea flavonol of Preparation Example 3 | 100 mg |
| Mannitol | 300 mg |
| Sterilized distilled water | 3000 mg |

[Formulation Example 7] Functional Drink

A functional drink was prepared according to a common method with to the composition described in Table 2.

TABLE 2

| Ingredients | Contents |
|---|---|
| Green tea extract of Preparation Example 1 | 1000 mg |
| Green tea polysaccharide of Preparation Example 2 | 100 mg |
| Green tea flavonol of Preparation Example 3 | 100 mg |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Folic acid | 50 μg |
| Calcium pantothenate | 0.5 mg |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |
| Purified water | 100 mL |

The invention claimed is:

1. A method for lowering blood heavy metal level, comprising administering an effective amount of a composition comprising a green tea extract, a green tea polysaccharide, and a green tea flavonol to a subject continuously exposed to a particulate matter atmosphere in need of lowering blood heavy metal level, wherein the blood heavy metal comprises lead and cadmium, wherein a weight ratio of the green tea extract, the green tea polysaccharide and the green tea flavonol is 10:0.1-3:0.01-9, wherein the green tea extract comprises catechin, and wherein a daily administration dosage of catechin by the green tea extract is 0.3-1.0 g.

2. The method according to claim 1, wherein the green tea extract is an extract of water, an organic solvent or a mixture solvent thereof.

3. The method according to claim 1, wherein the green tea flavonol comprises one or more selected from a group consisting of myricetin, quercetin and kaempferol.

4. The method according to claim 1, wherein the composition is a food composition.

5. The method according to claim 1, wherein the composition is a pharmaceutical composition.

* * * * *